United States Patent
Morita et al.

(10) Patent No.: US 11,576,653 B2
(45) Date of Patent: Feb. 14, 2023

(54) ULTRASONIC GENERATOR

(71) Applicant: NGK SPARK PLUG CO., LTD., Nagoya (JP)

(72) Inventors: Takeshi Morita, Saitama (JP); Kang Chen, Kashiwa (JP); Takashi Iijima, Tsukuba (JP); Takasuke Irie, Kunitachi (JP)

(73) Assignee: NGK SPARK PLUG CO., LTD., Nagoya (JP)

(*) Notice: Subject to any disclaimer, the term of this patent is extended or adjusted under 35 U.S.C. 154(b) by 14 days.

(21) Appl. No.: 17/108,529

(22) Filed: Dec. 1, 2020

(65) Prior Publication Data

US 2021/0169450 A1 Jun. 10, 2021

(30) Foreign Application Priority Data

Dec. 6, 2019 (JP) .............................. JP2019-220988

(51) Int. Cl.
*A61B 8/00* (2006.01)

(52) U.S. Cl.
CPC .......... *A61B 8/4483* (2013.01); *A61B 8/4272* (2013.01)

(58) Field of Classification Search
CPC ....... A61B 8/4483; A61B 8/4272; A61B 8/00; B06B 3/00; G10K 11/28
See application file for complete search history.

(56) References Cited

U.S. PATENT DOCUMENTS

| | | | |
|---|---|---|---|
| 8,021,305 B2 | 9/2011 | Itoh et al. | |
| 2008/0097217 A1 | 4/2008 | Itoh et al. | |
| 2015/0234265 A1* | 8/2015 | Takamatsu | G03B 21/142 353/31 |
| 2018/0147606 A1* | 5/2018 | Brouillette | G10K 11/28 |
| 2020/0316244 A1* | 10/2020 | Sustrick | G02B 5/0891 |
| 2022/0275926 A1* | 9/2022 | Li | F21V 7/00 |

FOREIGN PATENT DOCUMENTS

WO WO-2006/028249 A1 3/2006

OTHER PUBLICATIONS

Christensen, J., Fernandez-Dominguez, A., de Leon-Perez, F. et al. Collimation of sound assisted by acoustic surface waves. Nature Phys 3, 851-852 (2007). https://doi.org/10.1038/nphys774 (Year: 2007).*

* cited by examiner

*Primary Examiner* — Pascal M Bui Pho
*Assistant Examiner* — Michael Yiming Fang
(74) *Attorney, Agent, or Firm* — Leason Ellis LLP; Melvin C. Garner; Mitsuhiro Haraguchi

(57) ABSTRACT

An ultrasonic generator includes an ultrasonic wave source and a converging portion. The converging portion includes a first reflecting portion which reflects the ultrasonic wave generated by the ultrasonic wave source on its first reflecting surface, a second reflecting portion which reflects the ultrasonic wave reflected by the first reflecting surface on its second reflecting surface, and a waveguide serving as a transmission path for the ultrasonic wave. The waveguide is disposed such that the ultrasonic wave reflected by the second reflecting surface is introduced through an introduction portion thereof. The focal point of the second reflecting surface and the focal point of the first reflecting surface are disposed such that the ultrasonic wave reflected by the second reflecting surface becomes a plane wave.

4 Claims, 10 Drawing Sheets

ULTRASONIC GENERATOR

This application claims the benefit of Japanese Patent Application No. 2019-220988 filed Dec. 6, 2019, which is incorporated herein by reference in its entirety.

FIELD OF THE INVENTION

The present invention relates to an ultrasonic generator.

BACKGROUND OF THE INVENTION

Ultrasonic waves are presently used in various fields of application such as diagnosis and medical treatment. WO2006/028249 discloses an ultrasonic probe and an ultrasonograph, which are examples of techniques that utilize ultrasonic waves. The ultrasonic probe disclosed in WO2006/028249 includes an ultrasonic wave source for generating an ultrasonic wave, an ultrasonic wave transmission member for transmitting the ultrasonic wave generated by the ultrasonic wave source, and a direction changing means for changing the direction of the ultrasonic wave beam transmitted by the ultrasonic wave transmission member.

PRIOR ART DOCUMENT

Patent Document

[Patent Document 1] WO2006/028249

Problems to be Solved by the Invention

Incidentally, in a situation where use of an ultrasonic generator is demanded, transmission of ultrasonic waves through use of a waveguide, such as an ultrasonic waveguide tube, is sometimes desirable. The inventor of the present invention has conceived, as a structure which can meet such a demand, a structure in which an ultrasonic wave generated by an ultrasonic wave source disposed outside a waveguide is converged by a converging unit disposed outside the waveguide, and the converged ultrasonic wave is introduced into the waveguide. However, since merely converging an ultrasonic wave and introducing the converged ultrasonic wave into the waveguide results in great attenuation of the ultrasonic wave within the waveguide, it is difficult to transmit a stronger ultrasonic wave to a further point within the waveguide. The inventor of the present invention has also conceived another structure in which an ultrasonic wave source is disposed at a desired position within a waveguide. Since this structure allows the ultrasonic wave source to be disposed within the waveguide such that the ultrasonic wave source is located close to the position of an object to which the ultrasonic wave is to be transmitted, the above-described attenuation can be reduced. However, in the case where the ultrasonic wave source is disposed inside the waveguide, the sizes and structures of the ultrasonic wave source and peripheral components are restricted by the waveguide.

The present invention has been accomplished to solve at least one of the above-described problems, and an object of the present invention is to provide an ultrasonic generator which can transmit an ultrasonic wave by using a waveguide and in which a structure that can suppress attenuation of the ultrasonic wave within the waveguide is realized by a structure in which the size and structure of the ultrasonic wave source are less likely to be restricted by the waveguide.

SUMMARY OF THE INVENTION

Means for Solving the Problems

An ultrasonic generator which is one aspect of the present invention includes an ultrasonic wave source that is configured to generate an ultrasonic wave, and a converging portion that is configured to converge the ultrasonic wave generated by the ultrasonic wave source. The converging portion includes a first reflecting portion which has a first reflecting surface and reflects the ultrasonic wave generated by the ultrasonic wave source on the first reflecting surface; a second reflecting portion which is disposed opposite to the first reflecting surface, has a second reflecting surface, and reflects, the ultrasonic wave reflected by the first reflecting surface on the second reflecting surface; and a waveguide having an introduction portion which is disposed such that the ultrasonic wave reflected by the second reflecting surface is introduced into the waveguide through the introduction portion, said waveguide serving as a transmission path for the ultrasonic wave. Each of the first reflecting surface and the second reflecting surface has a paraboloidal surface. A focal point of the second reflecting surface and a focal point of the first reflecting surface are disposed such that the ultrasonic wave reflected by the second reflecting surface becomes a plane wave.

In the above-described ultrasonic generator, the ultrasonic wave source can be disposed outside the waveguide, and the ultrasonic wave from the ultrasonic wave source can be introduced into the waveguide after being converged by the converging portion. Therefore, in the ultrasonic generator, the size and structure of the ultrasonic wave source are less likely to be restricted by the waveguide as compared with a structure in which an ultrasonic wave source is disposed inside the waveguide. In addition, since the above-described ultrasonic generator can introduce the ultrasonic wave into the waveguide as a plane wave, attenuation of the ultrasonic wave within the waveguide can be suppressed. In the present specification, the plane wave means a wave whose transmission directions are directed in the same direction.

In the above-described ultrasonic generator, the ultrasonic wave source may be annularly disposed around the second reflecting surface such that the ultrasonic wave source faces the first reflecting surface. Moreover, the first reflecting surface may be annularly disposed around the introduction portion of the waveguide.

In the above-described ultrasonic generator, the structure capable of converting the ultrasonic wave generated by the ultrasonic wave source that is larger in size, to a plane wave and introducing the plane wave to the narrow waveguide can be realized by an efficient arrangement which restrains an increase in the size of the entire apparatus.

In the above-described ultrasonic generator, the paraboloidal surface is a revolving paraboloidal surface.

In the above-described ultrasonic generator, the structure that can converge the ultrasonic wave from the ultrasonic wave source and introduce the converged ultrasonic wave into the waveguide as a plane wave can be realized by a compact configuration using the first reflecting surface and the second reflecting surface which are disposed to face each other and are revolving paraboloidal surfaces.

In the above-described ultrasonic generator, the ultrasonic wave source may operate to generate the ultrasonic wave at a frequency of 30 kHz or higher.

The above-described ultrasonic generator can be utilized for applications in which a frequency of 30 kHz or higher is suitable. Also, in the case where the frequency of the ultrasonic wave generated by the ultrasonic wave source is 30 kHz or higher, energy concentration can be increased as compared with the case where the frequency is lower than 30 kHz, and a stronger effect can be easily applied by the ultrasonic wave.

Effect of the Invention

In the ultrasonic generator according to the present invention, a structure that can suppress attenuation of the ultrasonic wave within the waveguide can be realized by a structure in which the size and structure of the ultrasonic wave source are less likely to be restricted by the waveguide.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIG. 9 is a graph showing the results of a first simulation and showing the relation between phase difference and r/a.

DETAILED DESCRIPTION OF THE INVENTION

1. First Embodiment 1-1. Structure of Ultrasonic Generator

Figure 1:
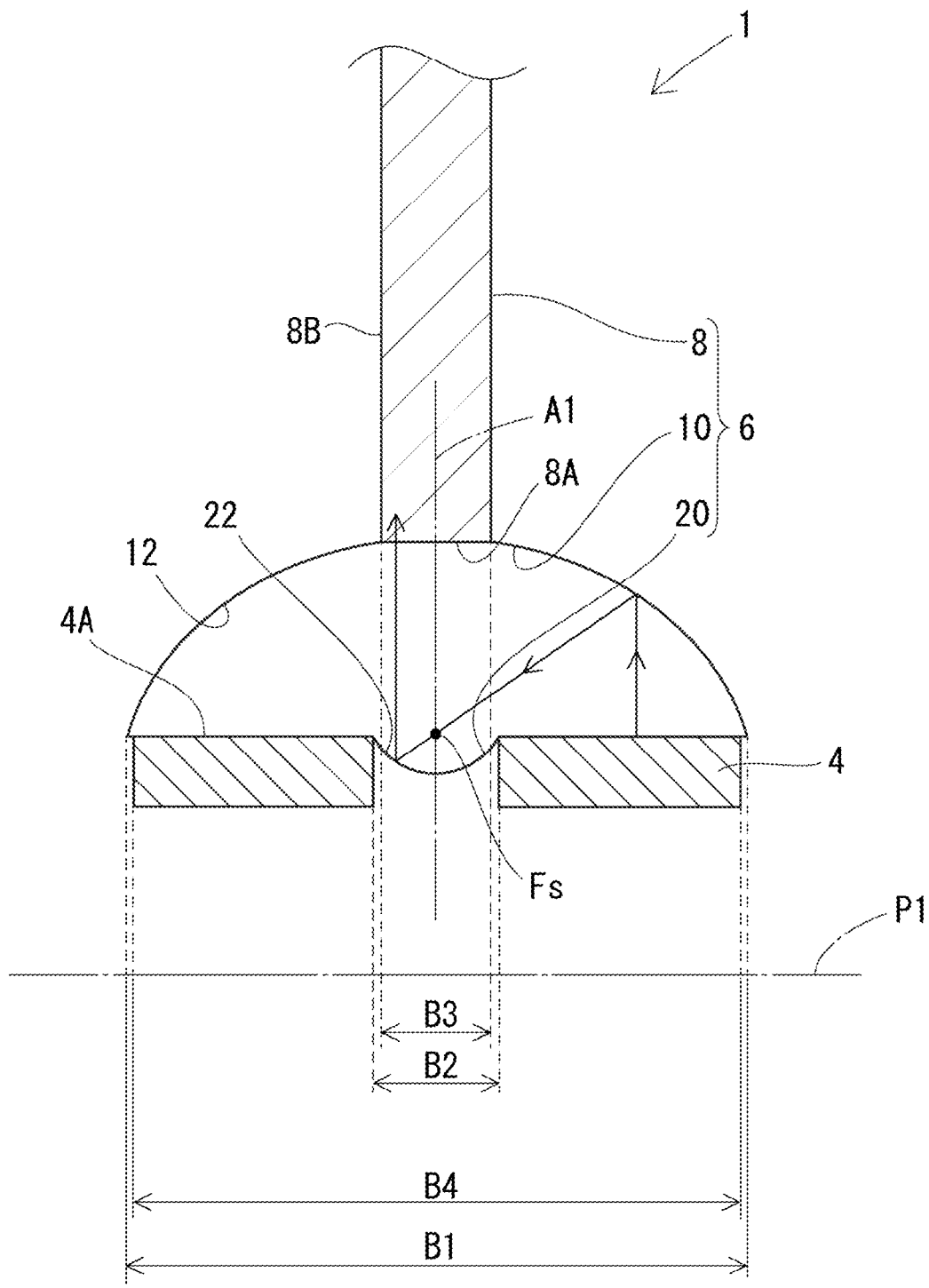
FIG. 1 is a schematic sectional view illustrating an ultrasonic generator according to a first embodiment.

An ultrasonic generator 1 shown in FIG. 1 is an apparatus for generating ultrasonic waves and is used in, for example, an ultrasonic diagnosis apparatus, an ultrasonic treatment apparatus, and a cavitation generation apparatus.

The ultrasonic generator 1 includes an ultrasonic wave source 4 for generating an ultrasonic wave, and a converging portion 6 for converging the ultrasonic wave generated at the ultrasonic wave source 4.

The ultrasonic wave source 4 is composed of, for example, an ultrasonic wave generating element such as a transducer. However, the ultrasonic wave source 4 may be composed of a known ultrasonic wave generation device other than the element, so long as the device is a means cable of generating an ultrasonic wave. The ultrasonic wave source 4 generates an ultrasonic wave as a plane wave propagating toward a first reflecting surface 12 along the direction of an axis A1. The ultrasonic wave source 4 generates an ultrasonic wave at a frequency of, for example, 30 kHz or higher.

The converging portion 6 is a device for converging the ultrasonic wave generated at the ultrasonic wave source 4 and transmitting the converged ultrasonic wave. The converging portion 6 includes a first reflecting portion 10, a second reflecting portion 20, and a waveguide 8.

The first reflecting portion 10 is a reflector for reflecting the ultrasonic wave generated at the ultrasonic wave source 4 by the first reflecting surface 12. The first reflecting surface 12 is a surface of the first reflecting portion 10 on the side toward the ultrasonic wave source 4 and is a convex paraboloid bulging toward the waveguide 8 side. The first reflecting surface 12 is a paraboloid of revolution formed by rotating, about the axis A1, a parabola drawn on a predetermined imaginary plane passing through the axis A1 such that the center of the parabola coincides with the axis A1. The first reflecting portion 10 is desirably formed of a material which is small in loss in a frequency band of 30 kHz or higher. In the representative example shown in FIG. 1, the first reflecting portion 10 is formed of a metal (for example, duralumin), and the first reflecting surface 12 is formed as a surface of the metal.

The first reflecting surface 12 is annularly disposed around an introduction portion 8A of the waveguide 8, which will be described later. As shown in FIG. 1, the waveguide 8 has an end portion provided adjacent to the first reflecting surface 12, and the said end portion serves as the introduction portion 8A. The first reflecting surface 12 extends from the introduction portion 8A toward the radially outer side with respect to the axis A1 serving as the center.

The second reflecting portion 20 is a reflector disposed in opposition to the first reflecting surface 12. The second reflecting portion 20 has a second reflecting surface 22 which reflects the ultrasonic wave reflected by the first reflecting surface 12. The second reflecting surface 22 is a surface of the second reflecting portion 20 on the side toward the first reflecting surface 12 and is a paraboloid concaved toward the side opposite the waveguide 8 in the direction of the axis A1. The second reflecting surface 22 is a paraboloid of revolution formed by rotating, about the axis A1, a parabola drawn on a predetermined imaginary plane passing through the axis A1 such that the center of the parabola coincides with the axis A1. The second reflecting portion 20 is desirably formed of a material which is small in loss in a frequency band of 30 kHz or higher. In the representative example shown in FIG. 1, the second reflecting portion 20 is formed of a metal (for example, duralumin), and the second reflecting surface 22 is formed as a surface of the metal.

The waveguide 8 is a portion serving as a transmission path for the ultrasonic wave. The waveguide 8 is formed into the shape of a solid column. The waveguide 8 is disposed such that the ultrasonic wave reflected by the second reflecting surface 22 is introduced into the interior of the waveguide 8 through the introduction portion 8A. The introduction portion 8A is an end portion of the waveguide 8 and has an exposed surface located adjacent to the first reflecting surface 12. The waveguide 8 introduces the ultrasonic wave into the interior thereof through the said exposed surface serving as an introduction surface. The outer edge of the exposed surface, which is the surface of the introduction portion 8A, has, for example, a circular shape. Further, the exposed surface of the introduction portion 8A is flat. The waveguide 8 has a rod portion 8B extending from the introduction portion 8A along the direction of the axis A1. The rod portion 8B is a solid rod portion whose outer circumferential surface is a cylindrical surface having a center on the axis A1, and the axial center of the rod portion 8B is the axis A1. The waveguide 8 is disposed such that the ultrasonic wave, which is a plane wave and is introduced from the introduction portion 8A, propagates through the rod portion 8B. As a result, the ultrasonic wave introduced from the introduction portion 8A propagates through a path along the rod portion 8B. No particular limitation is imposed on a destination to which the waveguide 8 guides the ultrasonic wave, and the destination may be in a living body or another region.

As shown in FIG. 1, in the ultrasonic generator 1, the ultrasonic wave source 4 is disposed to face the first reflecting surface 12. Specifically, a facing surface 4A, which is a surface of the ultrasonic wave source 4 on one side thereof faces the first reflecting surface 12.

Figure 2:
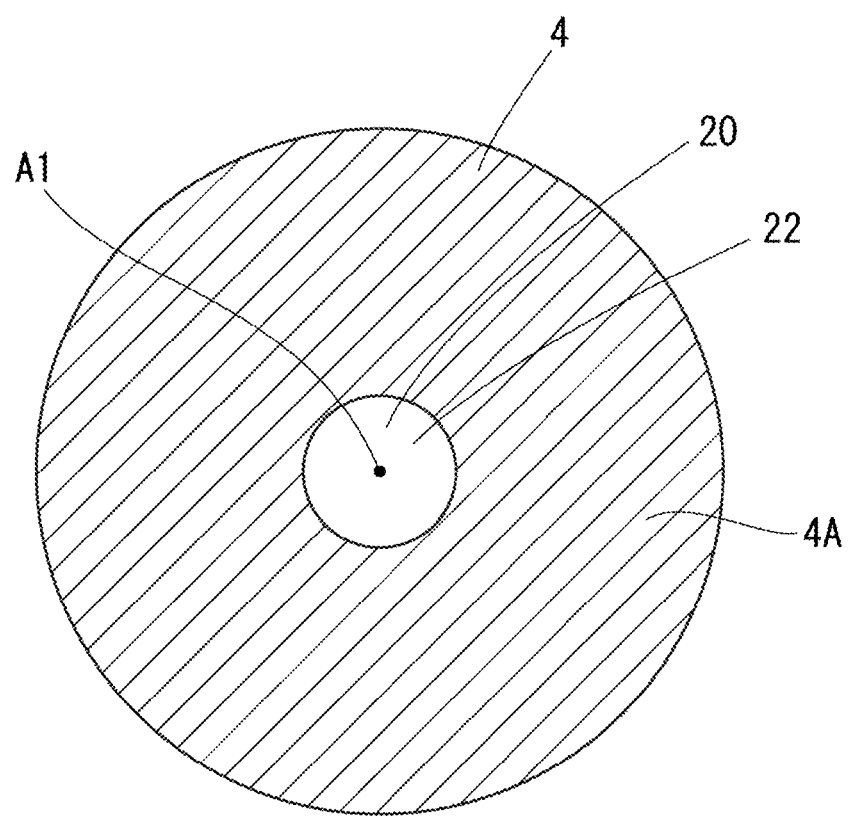
FIG. 2 is a plan view of an ultrasonic wave source and a second reflecting portion in the ultrasonic generator of FIG. 1 as viewed in the direction of an axis A1.

As shown in FIG. 2, the ultrasonic wave source 4 is annularly disposed around the second reflecting surface 22 such that the ultrasonic wave source 4 faces the first reflecting surface 12. Accordingly, the ultrasonic wave source 4 can emit ultrasonic waves, from a region around the second reflecting surface 22, in a direction along the axis A1. The ultrasonic wave source 4 has a predetermined thickness and has a plate-like shape.

Figure 3:
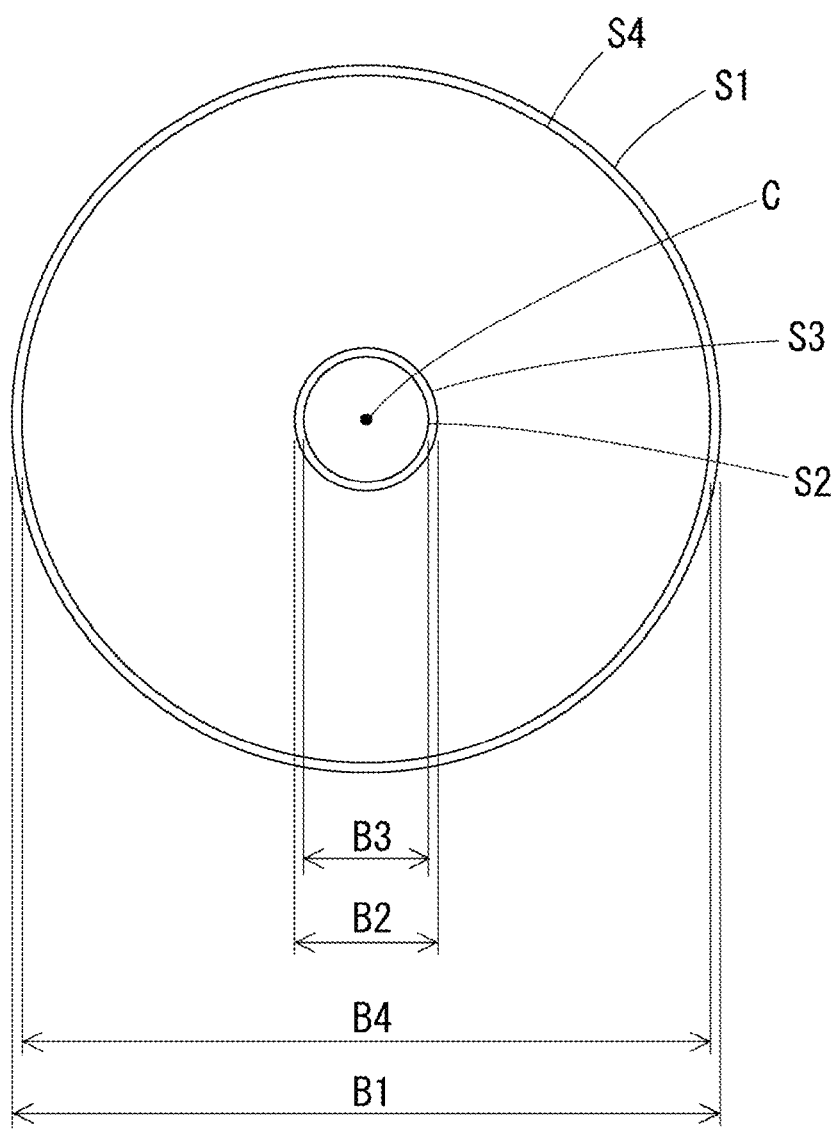
FIG. 3 is an explanatory view used for describing the relation among the outer edges of a first reflecting surface, a second reflecting surface, an introduction portion, and a facing surface as projected onto a projection plane orthogonal to the axis A1.

FIG. 3 shows the relation among the outer edges of the first reflecting surface 12 (FIG. 1), the second reflecting surface 22 (FIG. 1), the introduction portion 8A (FIG. 1), and the facing surface 4A (FIG. 1) as projected onto a projection plane P1 (FIG. 1). The projection plane P1 is an imaginary plane orthogonal to the axis A1 of the second reflecting surface 22. In FIG. 1, the projection plane P1 is shown by an alternate long and short dash line. A projected figure of the first reflecting surface 12 formed as a result of parallel projection of the first reflecting surface 12 onto the projection plane P1 will be referred to as a first projected figure. In FIG. 3, the outer edge of the first projected figure is denoted by symbol S1. A projected figure of the second reflecting surface 22 formed as a result of parallel projection of the second reflecting surface 22 onto the projection plane P1 will be referred to as a second projected figure. In FIG. 3, the outer edge of the second projected figure is denoted by symbol S2. A projected figure of the introduction portion 8A formed as a result of parallel projection of the introduction portion 8A onto the projection plane P1 will be referred to as a third projected figure. In FIG. 3, the outer edge of the third projected figure is denoted by symbol S3. A projected figure of the facing surface 4A of the ultrasonic wave source 4 formed as a result of parallel projection of the facing surface 4A onto the projection plane P1 will be referred to as a fourth projected figure. In FIG. 3, the outer edge of the fourth projected figure is denoted by symbol S4. In FIG. 3, a position where the projection plane P1 and the center axis A1 intersect each other is denoted by symbol C. In FIGS. 1 and 3, the diameter of the outer edge of the first projected figure is B1, the diameter of the outer edge of the second projected figure is B2, the diameter of the outer edge of the third projected figure is B3, and the diameter of the outer edge of the fourth projected figure is B4. The ultrasonic generator 1 illustrated in FIGS. 1 and 3 satisfies relations of B1>B2, B1>B3, B4>B2, and B4>B3. More specifically, the ultrasonic generator 1 satisfies a relation of B1>B4>B2>B3. In the example of FIG. 3, each of the outer edges of the first projected figure, the second projected figure, the third projected figure, and the fourth projected figure has a circular shape, and the diameters of the outer edges of the respective figures have the above-described relations.

1-2. Operation of Ultrasonic Wave Generation System

Figure 4:
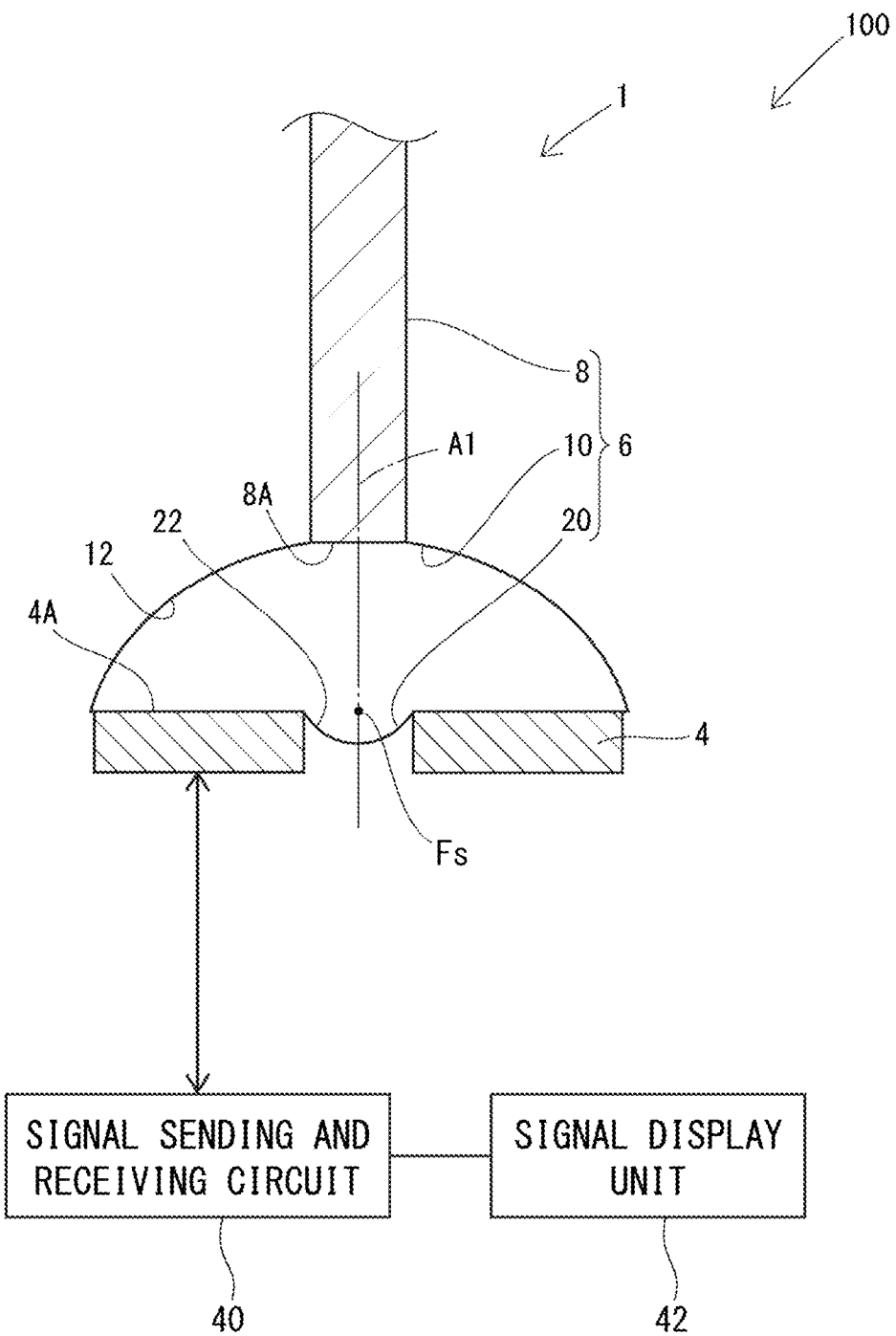
FIG. 4 is an explanatory view illustrating an ultrasonic wave generation system including the ultrasonic generator of FIG. 1.

FIG. 4 shows an example of an ultrasonic wave generation system 100 including the ultrasonic generator 1. The ultrasonic wave generation system 100 configured to function as an ultrasonic diagnosis apparatus includes a signal sending and receiving circuit 40 and a signal display unit 42 in addition to the ultrasonic generator 1. The ultrasonic wave generation system 100 applies the ultrasonic wave generated by the ultrasonic generator 1 to an object. The object reflects the ultrasonic wave. The ultrasonic wave generation system 100 converts the ultrasonic wave generated as a result of the reflection to an image signal and displays an image of the object.

The signal sending and receiving circuit 40 sends and receives ultrasonic waves through the ultrasonic wave source 4. The signal sending and receiving circuit 40 has a function of outputting an electrical signal (transmission signal) for causing the ultrasonic wave source 4 to generate an ultrasonic wave, and a function of receiving an electrical signal (reception signal) generated as a result of reception of an ultrasonic wave by the ultrasonic wave source 4. The transmission signal is a drive signal for driving the ultrasonic wave source 4, which is configured, for example, as a transducer, and the reception signal is an electrical signal generated when the ultrasonic wave source 4 configured as a transducer receives an ultrasonic wave.

The ultrasonic wave generation system 100 operates as follows. When a transmission signal is supplied from the signal sending and receiving circuit 40 to the ultrasonic wave source 4, the ultrasonic wave source 4 generates an ultrasonic wave in accordance with the transmission signal. The ultrasonic wave generated by the ultrasonic wave source 4 is a plane wave propagating in the direction of the axis A1. In the converging portion 6, the ultrasonic wave generated by the ultrasonic wave source 4 is reflected by the first reflecting surface 12, so that the ultrasonic wave converges toward the focal point (point Fs) of the first reflecting surface 12. After having passed through a region near the point Fs, the ultrasonic wave is reflected by the second reflecting surface 22.

In the converging portion 6, the focal point of the second reflecting surface 22 and the focal point of the first reflecting surface 12 are disposed such that the ultrasonic wave reflected by the second reflecting surface 22 becomes a plane wave. Specifically, the focal point of the second reflecting surface 22 coincides with the focal point of the first reflecting surface 12 at the point Fs. Namely, the point Fs is the focal point of the second reflecting surface 22 and the focal point of the first reflecting surface 12. By virtue of such a configuration, the ultrasonic wave reflected by the first reflecting surface 12 and focused to converge toward the point Fs is reflected by the second reflecting surface 22 and becomes a plane wave. The ultrasonic wave having been reflected by the second reflecting surface 22 and become a plane wave passes through the introduction portion 8A and enters the waveguide 8. The ultrasonic wave having entered the waveguide 8 is transmitted through the waveguide 8 and is applied to the object. The ultrasonic wave applied to the object is reflected by the object. The ultrasonic wave reflected by the object and carrying an image information of the object returns through the waveguide 8 and is received by the ultrasonic wave source 4. Upon reception of the ultrasonic wave by the ultrasonic wave source 4, an electrical signal corresponding to the ultrasonic wave received by the ultrasonic wave source 4 is received by the signal sending and receiving circuit 40, and the image information contained in the received signal is displayed by the signal display unit 42. The technique of displaying an image on the basis of the ultrasonic wave received by the ultrasonic wave source 4 (the ultrasonic wave containing the image information) may be a known technique used in, for example, an ultrasonic diagnosis apparatus.

1-3. Simulation

The following description relates to the results of simulations performed for the ultrasonic generator 1 and comparative examples.

In the simulations, the structures shown in FIGS. 5 to 8 were used.

Figure 5:
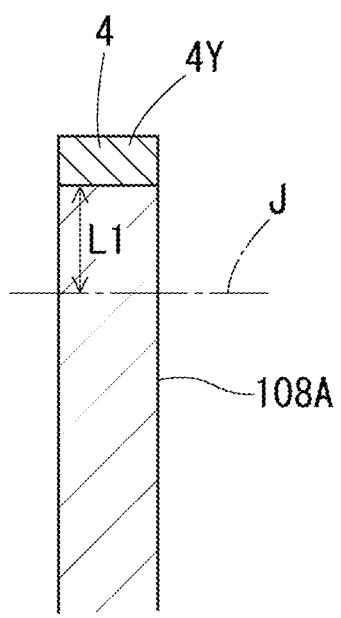
FIG. 5 is an explanatory view illustrating a first structure regarding a first comparative example compared with the embodiment in simulations.

In the structure shown in FIG. 5, an element 4Y serving as the ultrasonic wave source 4 is attached directly to a waveguide 108A such that the element 4Y covers an end portion of the waveguide 108A. In the structure shown in FIG. 5, the waveguide 108A is formed to have the shape of a solid column, and its one end portion functions as an ultrasonic wave introduction portion. In FIG. 5, a region of the element 4Y which does not face the end portion of the waveguide 108A is omitted. In the following description, the structure of FIG. 5 will be referred to as a first structure.

Figure 6:
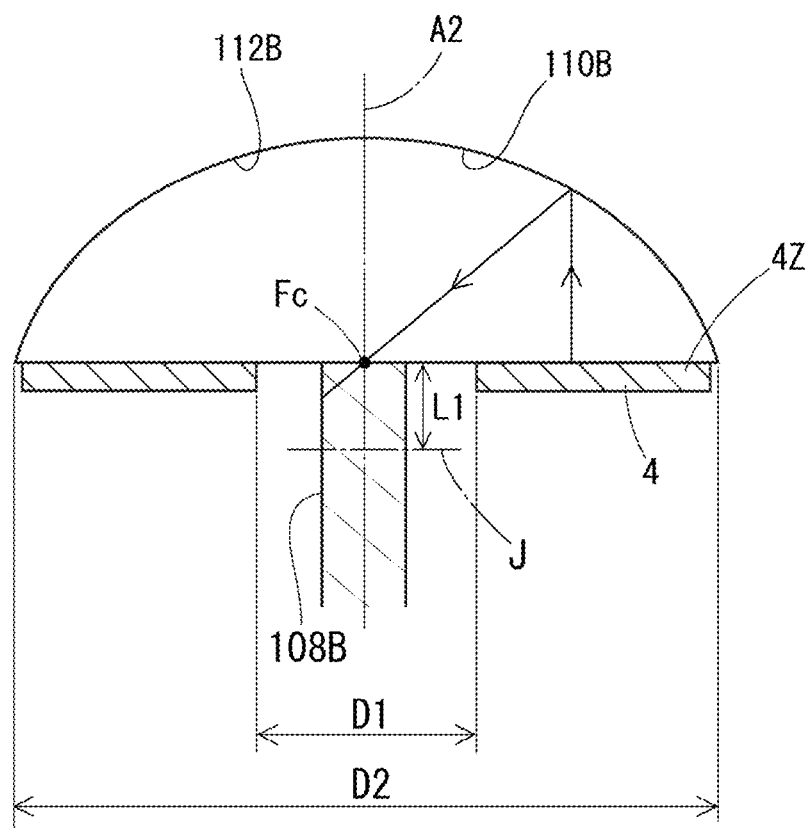
FIG. 6 is an explanatory view illustrating a second structure regarding a second comparative example compared with the embodiment in the simulations.

FIG. 6 shows an ultrasonic generator which includes a curved reflecting portion 110B like the first reflecting portion 10. In the ultrasonic generator of FIG. 6, the ultrasonic wave generated by the ultrasonic wave source 4 is reflected by a reflecting surface 112B which is a paraboloid of revolution similar to the first reflecting surface 12 (FIG. 1) and is introduced into the waveguide 108B. The waveguide 108B is formed to have the shape of a solid column, and its one end portion functions as an ultrasonic wave introduction portion, and the said end portion is located near the focal point Fc of the reflecting surface 112B. The waveguide 108B extends parallel to the axis A2 of the reflecting surface 112B. The center of the waveguide 108B coincides with the axis A2. In the structure of FIG. 6, the thickness of an element 4z serving as the ultrasonic wave source 4 is the same as that of the element 4Y shown in FIG. 5. The elements 4z used in the structures of FIGS. 6 to 8 have the same structure. Each element 4z has a structure similar to that of the ultrasonic wave source 4 shown in FIG. 1, and the outer diameter D2 and the inner diameter D1 of each element 4z differ from those of the ultrasonic wave source 4 shown in FIG. 1. The outer diameter D2 of each element 4Z is 40 mm, and the inner diameter D1 of each element 4Z is 16 mm. Each element 4z has the shape of an annular circular plate. In the structure of FIG. 6, the ultrasonic wave generated by the element 4Z reaches the reflecting surface 112B as a plane wave propagating along the axis A2. The ultrasonic wave is reflected once by the reflecting surface 112B, converges toward the focal point Fc, and enters the waveguide 108B. In the structures of FIGS. 5 to 8, the frequency of the ultrasonic wave source 4 is 1.45 MHz. In the following description, the structure of FIG. 6 will be referred to as a second structure.

Figure 7:
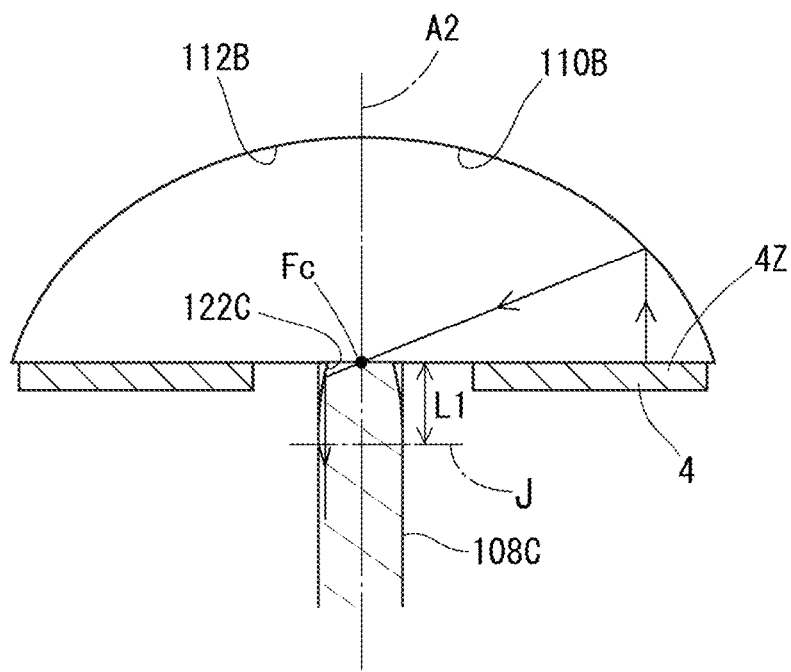
FIG. 7 is an explanatory view illustrating a third structure regarding a third comparative example compared with the embodiment in the simulations.

The structure of FIG. 7 differs from the structure of FIG. 6 only in the point that a reflecting surface 122C is provided. Specifically, a waveguide 108C used in the structure of FIG. 7 differs from the waveguide 108B used in the structure of FIG. 6 only in the point that the reflecting surface 122C is provided. The reflecting surface 122C is a reflecting surface (paraboloid of revolution) for converting the ultrasonic wave reflected by the reflecting surface 112B to a plane wave and guiding the plane wave to an inner part of the waveguide 108C. In the structure of FIG. 7 as well, the ultrasonic wave generated by the ultrasonic wave source 4 (specifically, the element 4Z) is reflected by the reflecting surface 112B, which is also a paraboloid of revolution similar to the first reflecting surface 12 (FIG. 1), and is introduced into the waveguide 108C. However, a portion of the ultrasonic wave reflected by the reflecting surface 112B is converted to a plane wave by the reflecting surface 122C. In the following description, the structure of FIG. 7 will be referred to as a third structure.

Figure 8:
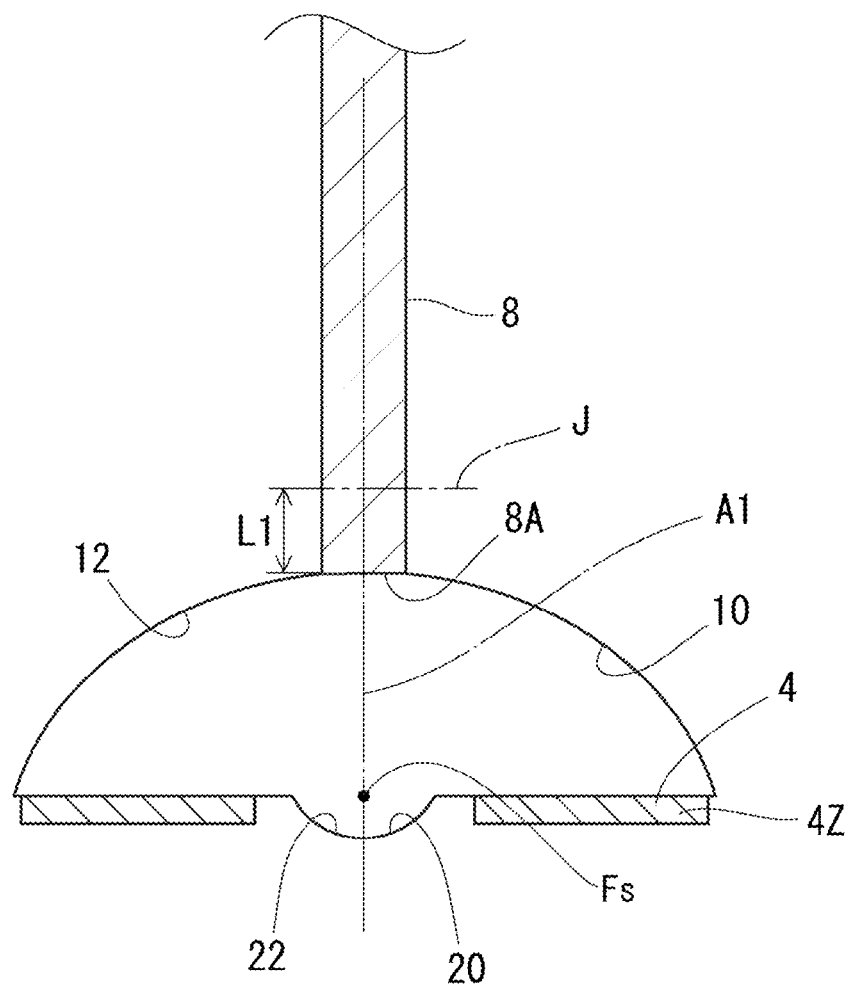
FIG. 8 is an explanatory view illustrating a fourth structure which is one form of the first embodiment.

The structure of FIG. 8 is the same as that of the ultrasonic generator 1 shown in FIG. 1. In the following description, the structure of FIG. 8 will be referred to as a fourth structure. In the structure of FIG. 8, the ultrasonic wave source 4 is the element 4Z used in the structures of FIGS. 6 and 7, and the shape and diameter of the waveguide 8 are the same as those of the waveguides 108A and 108B used in FIGS. 5 and 6 and those of a portion of the waveguide 108C used in FIG. 7, the portion being located on the inward side with respect to the reflecting surface 122C.

Figure 9:
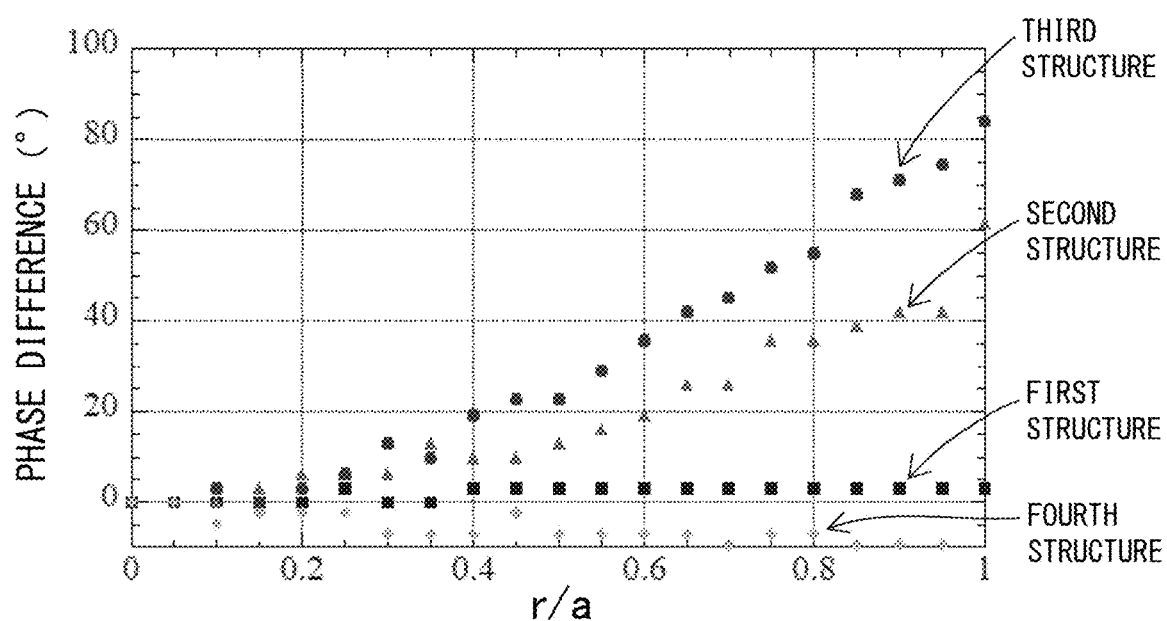

In the first simulation, for each of the four types of ultrasonic generators shown in FIGS. 5 to 8, a phase difference at an imaginary plane J (see FIGS. 5 to 8) spaced by a predetermined distance L1 from the end portion of the waveguide 108A, 108B, 108C, or 8 was calculated. In the first simulation, L1 is 1 mm. Specifically, in each of the first to fourth structures, the radius of the waveguide is represented by a, and the radial distance from the axial center of the waveguide on the imaginary plane J at the position of L1=1 mm is represented by r, wherein the axial center serves as an origin. In each of the first to fourth structures, the radius a is 1 mm. In the first simulation, the ratio of r/a was changed from 0 to 1, and a phase difference at each radial position on the imaginary plane J (for each value of the ratio of r/a) was obtained. The ratio of r/a is a value that specifies the position in the radial direction. The closer the ratio of r/a to 0, the closer to the axial center of the waveguide. The closer the ratio of r/a to 1, the closer to the outer circumferential surface of the waveguide. The phase difference at each position in the radial direction (each value of the ratio of r/a) is the difference between the phase of the ultrasonic wave at the position where r/a=0 (the center in the radial direction) and the phase of the ultrasonic wave at each position (each value of the ratio of r/a). FIG. 9 is a graph showing the results of the first simulation. In the graph of FIG. 9, the vertical axis represents the phase difference)(°), and the horizontal axis represents the position (r/a) representing the coordinate in the radial direction. As shown in FIG. 9, in the fourth structure (FIG. 8) corresponding to the first embodiment, even when the ratio of r/a increases, the phase difference does not increase, unlike the second structure shown in FIG. 6 and the third structure shown in FIG. 7. Namely, in the fourth structure, since the phase difference between an ultrasonic wave passing through a position near the outer circumferential surface of the waveguide and an ultrasonic wave passing through the center of the waveguide is small, attenuation is less likely to occur during propagation through the waveguide.

Figure 10:
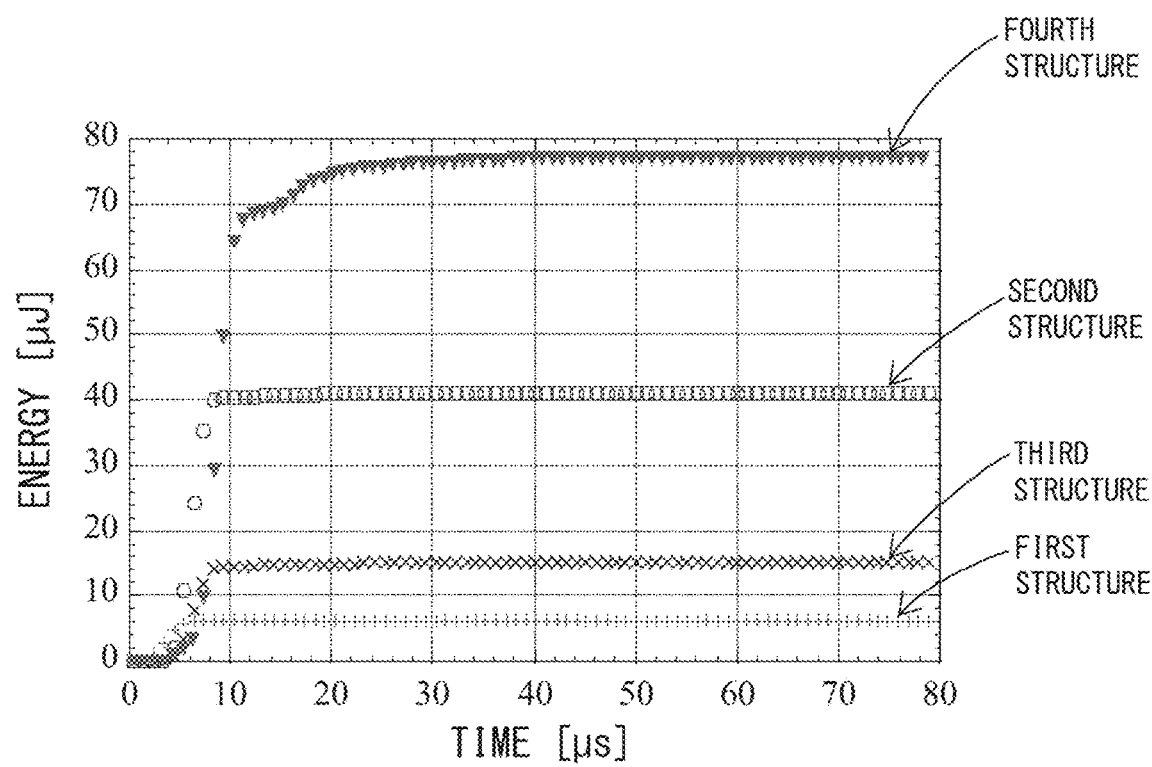
FIG. 10 a graph showing the results of a second simulation and showing the relation between energy and time.

In the second simulation, for each of the first to fourth structures, the energy at the imaginary plane J (see FIGS. 5 to 8) spaced by the predetermined distance L1 from the end portion of the waveguide 108A, 108B, 108C, or 8 was calculated. In the second simulation, the distance L1 is 5 mm. FIG. 10 is a graph showing the results of the second simulation. FIG. 10 shows the relation between time and energy at the imaginary plane J (see FIGS. 5 to 8) for each of the first to fourth structures. In the graph of FIG. 10, the vertical axis represents the energy at the imaginary plane J (see FIGS. 5 to 8) in each of the first to fourth structures, and the horizontal axis represents the time elapsed after the start of drive of the ultrasonic wave source in each of the first to fourth structures. In the simulation whose results are shown in FIG. 10, the distance L1 from the end portion of the waveguide to the imaginary plane J is 5 mm in each of the first to fourth structures. As shown in FIG. 10, it was confirmed that, in the case of the fourth structure (FIG. 8) corresponding to the first embodiment, as compared with the first to third structures, high energy can be obtained even at the imaginary plane J which is set back somewhat from the end portion of the waveguide.

1-4. Example of Action and Effect of Ultrasonic Generator

In the ultrasonic generator 1, the ultrasonic wave source 4 can be disposed outside the waveguide 8, and the ultrasonic wave from the ultrasonic wave source 4 can be introduced into the waveguide 8 after being converged by the converging portion 6. Therefore, unlike the structure in which an ultrasonic wave source is disposed inside the waveguide 8, in the ultrasonic generator 1, the size and structure of the ultrasonic wave source 4 are less likely to be restricted by the waveguide 8. Specifically, in the ultrasonic generator 1, the size of the ultrasonic wave source 4 can be increased easily, and a stronger ultrasonic wave can be easily introduced into the waveguide 8. In addition, since the ultrasonic generator 1 can introduce the ultrasonic wave into the waveguide 8 as a plane wave, attenuation of the ultrasonic wave within the waveguide 8 can be suppressed.

In the ultrasonic generator 1, the ultrasonic wave source 4 is annularly disposed around the second reflecting surface 22 such that the ultrasonic wave source 4 faces the first reflecting surface 12. The first reflecting surface 12 is annularly disposed around the introduction portion 8A of the waveguide 8. Therefore, in the ultrasonic generator 1, the structure capable of converting the ultrasonic wave source 4 that is larger in size, to a plane wave and introducing the plane wave to the narrow waveguide 8 can be realized by an efficient arrangement which restrains an increase in the size of the entire apparatus.

The ultrasonic generator 1 can be utilized for applications in which a frequency of 30 kHz or higher is suitable. Also, in the case where the frequency of the ultrasonic wave generated by the ultrasonic wave source 4 is 30 kHz or higher, energy concentration can be increased as compared with the case where the frequency is lower than 30 kHz, and a stronger effect can be easily applied by the ultrasonic wave.

Other Embodiments

The present disclosure is not limited to the embodiment described by the above description with reference to the drawings. Any combination of the features of the above-described embodiment and embodiments described below is possible so long as inconsistency does not occur. Also, any of the features of the above-described embodiment and embodiments described below may be omitted unless it is clearly described to be essential. Further, the feature of the above-described embodiment may be modified as follows.

In the above-described embodiment, as shown in FIG. 4, the ultrasonic wave generation system 100 is configured as an ultrasonic diagnosis apparatus. However, the ultrasonic wave generation system 100 may be an ultrasonic treatment apparatus. Alternatively, the ultrasonic wave generation system 100 may be a cavitation generation apparatus which applies an ultrasonic wave to an object (for example, liquid) to thereby generate a cavitation such as air bubbles.

In the first embodiment, as shown in FIG. 3, the ultrasonic generator is configured such that the outer edge S4 of the fourth projected figure is located on the inner side of the outer edge S1 of the first projected figure in the projection plane P1. However, the ultrasonic generator may be configured such that the outer edge S4 of the fourth projected figure is located on the outer side of the outer edge S1 of the first projected figure in the projection plane P1.

In the first embodiment, as shown in FIG. 3, the ultrasonic generator is configured such that the outer edge S2 of the second projected figure is located on the inner side of the outer edge S3 of the third projected figure in the projection plane P1. However, the ultrasonic generator may be configured such that the outer edge S3 of the third projected figure is located on the outer side of the outer edge S2 of the second projected figure in the projection plane P1.

Notably, the embodiments disclosed this time should be considered to be illustrative and not to be restrictive in all aspects. The scope of the present invention is not limited to the embodiments disclosed this time, and it is intended that the present invention encompasses all modifications within the range shown by the claims and the range of equivalents of the claims.

DESCRIPTION OF SYMBOLS

1: ultrasonic generator
4: ultrasonic wave source
4A: facing surface
6: converging portion
8: waveguide
8A: introduction portion
10: first reflecting portion
12: first reflecting surface
20: second reflecting portion
22: second reflecting surface
A1: axis (axis of first reflecting surface, axis of second reflecting surface)
P1: projection plane

The invention claimed is:
1. An ultrasonic generator comprising:
an ultrasonic wave source that is configured to generate an ultrasonic wave in an axial direction;
a first reflecting portion which has a first reflecting surface that reflects the ultrasonic wave generated by the ultrasonic wave source;
a second reflecting portion which is disposed opposite to the first reflecting surface in the axial direction and has a second reflecting surface that faces the first reflecting surface and reflects the ultrasonic wave reflected by the first reflecting surface; and
a waveguide having an introduction portion which is disposed such that the ultrasonic wave reflected by the second reflecting surface is introduced into the wave- guide through the introduction portion, said waveguide serving as a transmission path for the ultrasonic wave, wherein each of the first reflecting surface and the second reflecting surface has a paraboloidal surface, and wherein a focal point of the second reflecting surface and a focal point of the first reflecting surface are disposed such that the ultrasonic wave reflected by the second reflecting surface becomes a plane wave.

2. The ultrasonic generator according to claim 1, wherein the ultrasonic wave source is annularly disposed around the second reflecting surface such that the ultrasonic wave source faces the first reflecting surface, and the first reflecting surface is annularly disposed around the introduction portion of the waveguide.

3. The ultrasonic generator according to claim 1, wherein the paraboloidal surface of each of the first reflecting surface and the second reflecting surface is a revolving paraboloidal surface.

4. The ultrasonic generator according to claim 1, wherein the ultrasonic wave source generates the ultrasonic wave at a frequency of 30 kHz or higher.

\* \* \* \* \*